United States Patent [19]

Laridon et al.

[11] E Re. 30,107

[45] Reissued Oct. 2, 1979

[54] THERMOGRAPHIC RECORDING PROCESS

[75] Inventors: Urbain L. Laridon, Wilrijk; Albert L. Poot, Kontich; Jozef F. Willems, Wilrijk, all of Belgium

[73] Assignee: AGFA-GEVAERT N.V., Mortsel, Belgium

[21] Appl. No.: 925,962

[22] Filed: Jul. 18, 1978

[44] Published under the second Trial Voluntary Protest Program on Feb. 17, 1976 as document No. B 457,547.

Related U.S. Patent Documents

Reissue of:

[64] Patent No.: 3,996,397
Issued: Dec. 7, 1976
Appl. No.: 457,547
Filed: Apr. 3, 1974

[30] Foreign Application Priority Data

Apr. 4, 1973 [GB] United Kingdom ..... 16166/73
Jun. 19, 1973 [GB] United Kingdom ..... 29073/73

[51] Int. Cl.[2] ..... B41M 5/12; B41M 5/18

[52] U.S. Cl. ..... 427/145; 427/148; 427/150; 428/457; 428/488; 428/913

[58] Field of Search ..... 427/145, 148, 150, 261; 428/457, 488, 913; 96/114.1

[56] References Cited

U.S. PATENT DOCUMENTS

| | | | |
|---|---|---|---|
| 2,129,242 | 9/1938 | Sheppard et al. | 96/65 |
| 2,663,657 | 12/1953 | Miller et al. | 428/537 |
| 3,108,896 | 10/1963 | Owen | 428/537 |
| 3,819,382 | 6/1974 | Konig et al. | 96/114.1 |
| 3,839,041 | 10/1974 | Hiller | 96/114.1 X |

FOREIGN PATENT DOCUMENTS

| | | |
|---|---|---|
| 1127344 | 4/1962 | Fed. Rep. of Germany . |
| 1129151 | 5/1962 | Fed. Rep. of Germany . |

*Primary Examiner*—Thomas J. Herbert, Jr.
*Attorney, Agent, or Firm*—William J. Daniel

[57] ABSTRACT

A recording process, wherein an organic reducing compound being present in a supported or self-supporting layer and corresponding to one of the following general formulae (I) and (II):

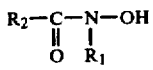

(I)

wherein:

$R_1$ represents hydrogen, an aliphatic group of a cycloaliphatic group, and $R_2$ represents an aliphatic oxy group, a cycloaliphatic oxy group, an aryloxy group, an amino group of the formula

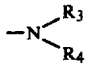

in which $R_3$ and $R_4$ (same or different) represent hydrogen, an aliphatic, a cycloaliphatic or an aromatic group or $R_3$ and $R_4$ represent together the necessary atoms to close a heterocyclic nitrogen containing nucleus;

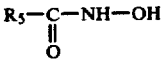

(II)

wherein $R_5$ represents an aliphatic, cycloaliphatic, aromatic or heterocyclic group, is caused to effect in said layer under the influence of information-wise heating an information-wise reduction of a reducible reaction partner.

11 Claims, No Drawings

THERMOGRAPHIC RECORDING PROCESS

Matter enclosed in heavy brackets [ ] appears in the original patent but forms no part of this reissue specification; matter printed in italics indicates the additions made by reissue.This invention is concerned with heat-sensitive materials suited for the recording and/or reproduction of information and to recording processes wherein such materials are used.

This invention is concerned with heat-sensitive materials suited for the recording and/or reproduction of information and to recording processes wherein such materials are used.

Heat-sensitive copy-sheets capable of undergoing a colour change by the thermally initiated reduction of a compound with an organic reducing compound are known, e.g., from the United Kingdom Patents No. 318,203 filed Aug. 16, 1929 by Marconi's Wireless Telegraph Co. and No. 866,076 filed June 28, 1957 by Minesota Mining and Manufacturing, from the German Patent No. 888,043 filed June 29, 1943 by Agfa AG and from the U.S. Pat. Nos. 2,129,242 of Samuel E. Sheppard and Waldemar Vanselow issued Sept. 6, 1938, 2,504,593 of Andre Schoen issued Apr. 18, 1950, 2,663,654 of Carl S. Miller and Bryce L. Clark issued Dec. 22, 1953 and 2,663,657 of Carl S. Miller and Bryce L. Clark issued Dec. 22, 1953.

A heat-sensitive copy-sheet containing said compounds is suited for the thermographic copying of originals containing infrared-absorbing image markings. When the original is exposed to infrared radiation in heat-conductive contact with such copy-sheet, the infra-red absorbing image portions of the original are selectively heated and by heat transfer cause the development in the heat-sensitive sheet of a visible image corresponding with the image markings of the original.

A problem to be solved in connection with thermographic recording materials resides in the difficulty to produce recording layers that are sufficiently stable in storage and still produce images having a sufficient optical density on a neutral image background.

It is an object of the present invention to provide a thermographic process in which an organic reducing compound by means of heat effects an information-wise reduction of a reaction partner in order to form a visible image.

It is another object of the present invention to provide thermographic recording materials having a good storage stability and that produce images of high optical density on a neutral image background.

More particularly the present invention relates to a heat-sensitive recording material comprising an organic reducing agent or mixture of reducing agents and (a) reaction partner(s) that with the aid of heat can form (a) coloured substance in an oxidation-reduction reaction with said reducing agent or mixture of reducing agents.

According to one embodiment the heat-sensitive recording material comprises the organic reducing agent in a recording element being a supported or self-supporting layer that contains in intimate admixture said reducing agent(s) and said reaction partner(s) distributed non-differentially through its composition.

According to another embodiment the heat-sensitive recording material comprises on a same support the organic reducing agent(s) and said reaction partner(s) kept apart in adjacent coatings from which they can reach each other during information-wise heating.

The organic reducing agent in said recording material corresponds to one of the following general formulae (I) and (II):

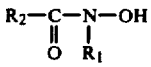

(I)

wherein:

$R_1$ represents hydrogen or an aliphatic group including a cycloaliphatic group and such groups in substituted form, e.g. an alkyl group containing from 1 to 4 carbon atoms, and $R_2$ represents an aliphatic or cycloaliphatic oxy group, e.g. an alkoxy group containing up to 18 carbon atoms, an aryloxy group e.g. a phenyloxy group, an amino group, a substituted amino group e.g. a

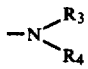

group in which $R_3$ and $R_4$ (same or different) represent hydrogen, an aliphatic, cycloaliphatic or aromatic group including said groups in substituted form e.g. an alkyl group, an alkenyl group, an allyl group, an aryl group e.g. a phenyl group or substituted phenyl group that carries substituents e.g. halogen such as fluorine, chlorine or bromine or alkyl containing e.g. up to 3 carbon atoms, alkoxy containing e.g. up to 3 carbon atoms or a nitrile group; or $R_3$ and $R_4$ together represent the necessary atoms to close a heterocyclic nitrogen containing nucleus, e.g. a piperidine morpholine or pyrrolidine nucleus;

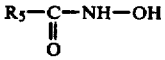

(II)

wherein:

$R_5$ represents an aliphatic, cycloaliphatic, aromatic or heterocyclic group preferably a phenyl group including said groups in substituted form.

Specific examples of reducing compounds according to one of said general formulae and that are particularly suitable for use in a thermally initiated reduction reaction are listed in the following table.

Table

| No of the compound | Structural formula | Melting point °C. |
|---|---|---|
| 1 | $H_5C_2O-CO-NH-OH$ | liquid at 20 |
| 2 | 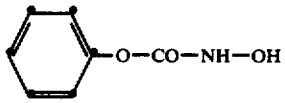 | & 111 |
| 3 | $H_2N-CO-NH-OH$ | 147.7 |
| 4 | $H_5C_2-NH-CO-NH-OH$ | & — |
| 5 | 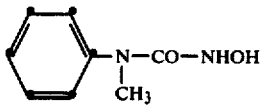 | & 92 |
| 6 | $H_{23}C_{11}-NH-CO-NH-OH$ | 75 |
| 7 | $H_{37}C_{18}-NH-CO-NH-OH$ | 121 |
| 8 | $H_2C-CH-CH_2-NH-CO-NH-OH$ | 113 |
| 9 | $H_{25}C_{12}-NH-CO-N(CH_3)(OH)$ | 79 |

Table-continued

| No of the compound | Structural formula | Melting point °C. |
|---|---|---|
| 10 | 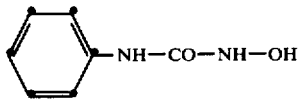 | 154 |
| 11 | 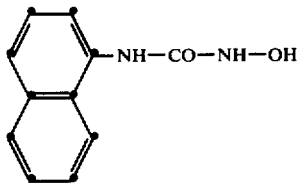 | 184 |
| 12 | 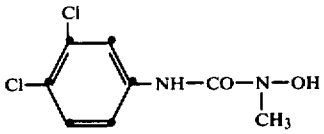 | 127 |
| 13 | 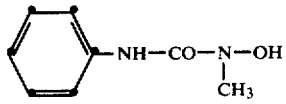 | 95 |
| 14 | 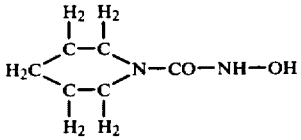 | 120 |
| 15 | 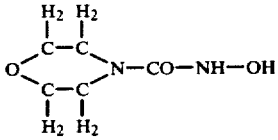 | 150 |
| 16 | 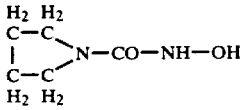 | 180 |
| 17 | $CH_3(CH_2)_3$—NH—CO—NH—OH | 130 |
| 18 | 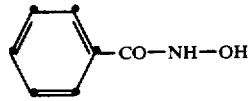 | 130 |

The preparation of the compounds having the general formula (I) is known e.g. from the published German Patent Applications No. 1,127,344 filed Feb. 18, 1960 and No. 1,129,151 filed Aug. 17, 1960 both by Badische Anilin- & Soda-Fabrik.

For illustrative purposes a preparation of the preferred compound 14 is given here in detail.

The preparation of compound 14 called 1-hydroxyaminocarbonyl-piperidine proceeded as follows:

1-chlorocarbonyl-piperidine was prepared by introducing 1 mole of phosgene into 500 ml of toluene at 5° C. Thereupon 1 mole of piperidine and 1 mole of pyridine were added dropwise to the phosgene solution at a temperature of 20° C. The precipitate of pyridine hydrochoride was sucked off, the toluene was removed by evaporation and the 1-chlorocarbonyl-piperidine was distilled under vacuum. Boiling point: 118° C. at 15 mm Hg. 1 mole of hydroxylamine hydrochloride was mixed with 500 ml of methanol whilst stirring. To the obtained mixture 0.3 mole of triethylamine were added at 10°-15° C. Thereupon a mixture of 1.7 mole of triethylamine and 1 mole of 1-chlorocarbonyl piperidine in 250 ml of methylene chloride were added dropwise at 10°-15° C. The stirring of the reaction mixture was continued for 1 hour and subsequently 2 moles of solid sodium hydroxide were added. The sodium chloride precipitate formed was sucked off and the filtrate was concentrated by evaporation the solvent. The concentrate was added to 1 liter of toluene at 100° C. The liquid was filtered, cooled down, and the crystalline 1-hydroxy-aminocarbonylpiperidine was separated and dried. Melting point: 120° C. N-hydroxyaminocarbonyl morpholine (compound 15) having a melting point of 150° C. was prepared analogously.

The preparation of compound 16 proceeded as follows: 1 mole of hydroxylamine hydrochloride were dissolved in 1 liter of methanol and 0.5 mole of triethylamine added to the obtained solution. Thereto 1 mole of 1-chlorocarbonyl-pyrrolidine and 1.5 mole of triethylamine dissolved in 20 ml of methylene chloride were added dropwise while keeping the reaction temperature at 15° C. Thereupon 2 moles of sodium hydroxide were added and the formed sodium chloride sucked off. The filtrate was concentrated by evaporation and the residue recrystallized from benzene.

Melting point of compound 16: 180° C.

The compound 18 (melting point: 130° C.), which is representative for the compounds according to the general formula (II), can be prepared in different ways by reaction of the corresponding acid chloride or carboxylic acid ester with hydroxylamine or by oxidation of the corresponding aldoxime (see e.g. Beilstein IX, 9, 301, and Erganzungsband 1, IX, 128 or Erganzungsband 2, IX, 213).

The organic reducing compound is used preferably in a supported layer or self-supporting sheet in intimate admixture with a reaction partner that on heating produces a visible colour change by reduction. Suitable reaction partners are described e.g. in the United Kingdom Patent No. 866,076 as mentioned above and the U.S. Pat. No. 3,108,896 of Richard Owen issued Oct. 29, 1963. As reaction partners noble metal compounds are preferred that through an oxidation reduction reaction are capable of setting free a metal.

Preferred noble metal compounds are silver compounds, which under the conditions encountered in thermographic copying, i.e. preferably in a temperature range of 60° to 200° C., are poorly light-sensitive, e.g. the silver salts of aliphatic carboxylic acids with a thioether group such as described, e.g., in the United Kingdom Patent No. 1,111,492 filed Aug. 13, 1965 by Agfa-Gevaert AG or silver salts of long chained aliphatic (at least $C_{13}$) carboxylic acids such as silver behenate, silver palmitate, silver stearate and others.

The effectiveness of the reduction obtained with the organic reducing agents of one of the above general formulae varies with the amount thereof. Useful results are obtained already with 0.25 mole of reducing agent per 1 mole of noble metal compound.

In addition to said image-forming reaction partners the recording element in which the visible image is formed may contain further additives e.g. toning agents and auxiliary reducing or developing agents.

As toning agents suited in the production of black or neutral grey noble metal images such as silver images, phthalazinone and its derivatives (see U.S. Pat. Nos. 3,074,809 of Richard Owen issued Jan. 22, 1963 and 3,446,648 of Wesley R. Workman issued May 27, 1969 and German Pat. Application P 2,220,618 filed Apr. 27, 1972 by Agfa-Gevaert AG and/or phthalimide compounds may be used.

The phthalimides preferably correspond to the following general formula:

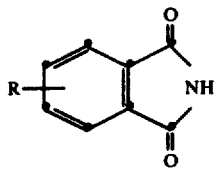

in which:

R represents a saturated or unsaturated aliphatic group or an alkoxy group, preferably having from 1 to 6 carbon atoms, a cycloalkyl group or cycloalkoxy group, e.g. cyclopentyl or cyclohexyl.

These compounds can be prepared according to processs known to those skilled in the art as described e.g. in Beilstein, Vol. 27, pp. 458 and 512, Vol. 27, 2, Erg. page 382, Vol. 21, p. 607, Vol. 2, Erg. pages 444 and 445, in Chemical Abstracts, Vol. 54, p. 8710 a–c (1960) and in the published German Patent Application No. 1,091,976 filed Oct. 2, 1958 by Farbenfabriken Bayer.

Other particularly suitable toning agents that may be used alone or in conjunction with said phthalazinones or phthalimide derivatives are described in the German Patent Applications Nos. P 2,261,739 filed Dec. 16, 1972 and P 2,328,145 filed June 2, 1973 both by Agfa-Gevaert AG and correspond to the following general formula:

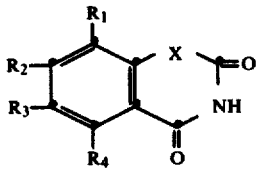

wherein:

X represents oxygen or a

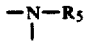

group wherein $R_6$ represents an alkyl group e.g. a $C_1$–$C_{20}$ alkyl group, preferably a —$CH_3$ or ethyl group, each of $R_1$, $R_2$, $R_3$and $R_4$ (same or different) represent hydrogen, alkyl e.g. $C_1$–$C_{20}$ alkyl, preferably $C_1$–$C_4$ alkyl, cycloalkyl, especially cyclopentyl or cyclohexyl, alkoxy, preferably $C_1$–$C_2$ alkoxy, alkylthio preferably $C_1$–$C_2$ alkylthio, hydroxy, dialkylamino in which the alkyl groups preferably are $C_1$–$C_2$ alkyl groups or halogen, preferably chlorine or bromine and wherein $R_1$ and $R_2$ or $R_2$ and $R_3$ or $R_3$ and $R_4$ may represent the necessary atoms to close a condensed aromatic ring, preferably a benzene ring.

As auxiliary reducing agents sterically hindered phenols that on heating become reactive partners in the reduction reaction, e.g. 2,6-ditert.butyl p-cresol and/or 2,6-dicyclohexyl-p-cresol, and certain bisphenols e.g. those of the U.S. Pat. No. 3,547,648 of Burt K. Sagawa issued Dec. 15, 1970, may be used.

In the recording materials of the present invention the reactants are preferably applied to a thin flexible carrier or backing such as paper, e.g. glassine paper or baryta-coated paper, or transparent film, e.g. consisting of a cellulose ester or polyethylene terephthalate, in admixture with a film-forming polymeric or resinous binder. The binder can yield a self-supporting sheet or tape when it has a sufficient mechanical strength.

The reactants may be supported in a fibrous web in the absence of a binder. Pigments, e.g. zinc oxide or titanium dioxide, fillers, meltable substances, e.g. waxes, dyes and various other additives may be included for obtaining special effects aimed at.

The reducible compound such as the noble metal salt and the reducing agent are preferably intermixed prior to coating, but may be applied in separate but contiguous layers from which the reducing agent can diffuse to the noble metal salt during the heating of the recording material.

As binding agent for the reducing compound and the compound thermally reducible therewith all kinds of natural, modified natural or synthetic resins may be used, e.g. proteins such as gelatin, cellulose derivatives, e.g. a cellulose ether such as ethylcellulose, cellulose esters, carboxymethylcellulose, alginic acid and derivatives, starch ethers, galactomannan, polyvinyl alcohol, poly-N-vinylpyrrolidone, polymers derived from $\alpha,\beta$-ethylenically unsaturated compounds, e.g. vinylhomo- and copolymers such as polyvinyl chloride, copolymers of vinyl chloride and vinyl acetate, partially saponified polyvinyl acetate, copolymers of acrylonitrile and acrylamide, polyacrylic acid esters, polymethacrylic acid esters or polyethylene.

Heat-sensitive recording materials of the present invention may be used in any process in which heat is applied information-wise to or generated in the recording material, e.g. by means of hot bodies for example a hot stylus or by means of heat-producing radiation, e.g. infrared radiation.

Heat-sensitive sheet-like recording materials of the present invention are particularly suited for the thermographic copying of originals containing infrared-absorbing image markings. When the original in contact with the present recording material is exposed to infrared radiation, the infrared-absorbing image portions of the original are heated selectively and by heat transfer cause the formation in the contacting heat-sensitive sheet of a visible colour change resulting from the reaction of the organic reducing agent with the reaction partner of the "oxidation-reduction colour reaction", e.g. a noble metal salt.

According to another exposure technique the recording material is heated information-wise or image-wise by radiation absorbed in the recording material. In order to improve the absorption of information-wise modulated radiation, which may be light and/or infrared radiation, the copying material in heat-conductive relationship with the oxidation-reduction partner(s) contains a certain amount of a substance or substances that are capable of converting absorbed electromagnetic radiation energy into heat. Suitable substances for that purpose are, e.g., heavy metal particles and finely divided carbon. For more details about such exposure technique and the use of these substances reference is made to the U.S. Pat. No. 3,476,937 of Marcel Nicolas Vrancken issued Nov. 4, 1969 and the United Kingdom Patent No. 1,160,221 filed May 17, 1965 by Gevaert Photo-Producten N.V.

Heat-sensitive recording materials of the present invention containing said noble metal salts are suitable for making direct, high-contrast, clear-detail, black permanent copies of typewritten, printed and other graphic subject matter. The recording materials are stable at room and normal storage temperatures, and may be stored in daylight without visible change either before or after heat-copying when no light-sensitive silver halide is present in their composition.

The thermographic recording materials may be applied in so-called "front-printing" as well as in "back printing". In front printing the radiant energy, e.g. from an infrared radiation source, is directed through a heat-sensitive copying paper to a printed original. Radiant energy is absorbed selectively in the printed areas of the original and released therefrom in the form of heat energy, causing a visible change in the areas of the recording material corresponding with the heated areas of the original.

In the "back printing" technique the radiant energy, e.g. from an infrared radiation source, is projected through the rear side of the printed surface of the printed original and the resulting release of heat energy causes a visible change in the heat-sensitive layer contacting the printed surface. Just as in the front printing method the visible change is produced in correspondence with the heated areas of the original. "Front printing" and "back printing" have been illustrated in the United Kingdom Patent 866,076 as mentioned above.

The following examples illustrate the present invention. The percentages and ratios are by weight unless otherwise indicated.

The recording materials of the present Examples obtain a colouration already at a temperature of 80° C. and are particulaly suited for recording techniques in which the information-wise heating of the recording material proceeds with a hot stylus.

EXAMPLE 1

A dispersion was obtained by ball-milling the following ingredients for 16 h:

| | | |
|---|---|---|
| butanone | 50 | ml. |
| after-chlorinated polyvinyl chloride | 5 | g |
| silver behenate | 2.5 | g |

Before coating a solution containing the following ingredients was added to 3 ml of the ball-milled composition:

| | |
|---|---|
| butanone | 3 ml |
| compound 10 of Table (melting point: 154° C.) | 0.02 g |
| 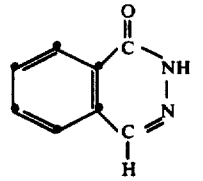 (phthalazinone as toning agent) | 0.01 g |

The coating of the final mixture was carried out on a polyethylene terephthalate support of 0.1 mm at a wet coating thickness of 75 μm.

The coated layer was dried at 60° C. for 5 min. The heat-sensitive layer of the obtained thermographic material was put into contact with a paper carrying a text printed with carbon ink and contact-exposed with infrared radiation in a THERMOFAX copying apparatus, Model 47-3M (a thermographic copying apparatus of Minnesota Mining & Manufacturing Company, St. Paul, Minn., U.S.A.). A black copy on a neutral image background was obtained.

Same results were obtained by replacing in said thermographic material the after-chlorinated polyvinyl chloride with one of the following binding agents:

copolymer of vinyl chloride and vinyl acetate
copolymer of vinylidene chloride and acrylonitrile
copolyester of iso- and terephthalic acid and 1,2-ethanediol.

By coating on the recording layer of the present example 1 a second binder layer consisting of ethylcellulose applied at a wet coating thickness of 50 μm from a solution of 5 g of ethylcellulose in 100 ml of ethanol, a much more optically clear image background was obtained after drying.

Same results were obtained by replacing silver behenate by silver stearate.

EXAMPLE 2

Example 1 was repeated with compound 18 of the Table in an amount of 0.05 g. A good result was obtained.

EXAMPLE 3

3 ml of the dispersion obtained in example 1 were mixed with a solution of 0.02 g of phthalazinone in 3 ml of butanone and coated at a wet coating thickness of 50 μm onto a polyethylene terephthalate support having a thickness of 0.1 mm. After drying that coating at 60° C. for 5 min. another coating was applied thereto at a wet coating thickness of 50 μm from a 5% solution of ethylcellulose in ethanol, which solution contained also 0.5 g of reducing compound 9 of the Table.

After drying and thermographical exposure of the recording material as described in example 1, a dense black copy of the original was obtained.

In said example 4 the ethylcellulose was replaced by the following binding agents applied from the following solvents;

after-chlorinated polyvinyl chloride applied from butanone
polyvinyl acetate applied from methanol
cellulose nitrate applied from methanol
polyvinyl butyral applied from a mixture of methanol and ethylene glycol monomethyl ether (9:1 by volume).

Equally good results were obtained.

EXAMPLE 4

In a ball-mill 50 g of silver behenate and 0.5 g of 3-nitro-phthalic acid were dispersed in 1000 ml of a 10% by weight solution of a copolymer of vinyl acetate and vinyl chloride (monomer ratio being 15/85 by weight) in butanone.

After 15 h of ball-milling a dispersion B was obtained.

To a polyester resin support of 0.10 mm the following coating composition was applied in a covering ratio of 80 g per sq.m.

| | |
|---|---|
| Dispersion B | 30 ml |
| 10% by weight solution in butanone of said copolymer of vinyl acetate and vinyl chloride | 15 ml |
| 5% by weight solution of phthalazinone as toning agent in butanone | 5 ml |
| 5% by weight solution of compound 14 in butanone | 10 ml |

After drying at 50° C., a second layer was applied to the dried layer in a covering ratio of 70 g per sq.m from a 2.5% by weight solution of ethylcellulose in a mixture of 90 ml of ethanol and 10 ml of acetic acid.

After drying at 50° C. the obtained transparent heat-sensitive recording material was exposed reflectographically in a common thermographic exposure apparatus with an infrared radiation source. During the exposure the layer containing compound 14 was held in direct contact with the infrared-absorbing black image markings of a printed text paper original.

The area of the recording material corresponding with the image-markings of the original turned black. The obtained copy was particularly suited for use as a transparency in an overhead projector.

EXAMPLE 5

In a ball-mill 50 g of silver behenate and 0.5 g of 3-nitro-phthalic acid as stabilizing agent were dispersed in 1000 ml of a 10% solution in butanone of after-chlorinated polyvinyl chloride.

After 15 h of ball-milling a dispersion A was obtained. Onto a polyester resin support of 0.10 mm the following coating composition was applied at covering rate of 80 g per. sq.m.

To a polyethylene terephthalate support of 0.075 mm the following coating composition was applied in a covering ratio of 70 g per sq.m.:

| | |
|---|---|
| dispersion A | 70 ml |
| butanone | 60 ml |
| 5% solution of phthalazinone in butanone | 10 ml |
| 5% solution of compound 18 in butanone | 20 ml |

After drying at 50° C. a second layer was applied to the dried layer from a 2.5% by weight solution of ethylcellulose in ethanol in a covering ratio of 80 g per sq.m.

After drying that second layer at 50° C. a transparent thermosensitive recording material was obtained.

The recording material was exposed reflectographically in a common thermographic exposure apparatus with infrared light source. During the exposure said protective coating was held in direct contact with the infra-red absorbing image markings of an original representing a printed text on paper.

The area of the recording material corresponding with the image-markings of the original turned black. The obtained copy was particularly suited for use as a transparency in an overhead projector.

EXAMPLE 6

Onto a polyethylene terephthalate support of 0.075 mm the following coating composition was applied at a covering rate of 70 g per sq.m.

| | |
|---|---|
| dispersion A (see example 5) | 70 ml |

-continued

| | |
|---|---|
| butanone | 60 ml |
| 5% solution of butanone of phthalaznone | 10 ml |
| 5% solution in butanone of compound 10 | 20 ml |

After drying at 50° C. the obtained recording material is image-wise exposed as described in Example 5.

A black image on a transparent base suited for projection with an overhead projector was obtained.

Analogous results were obtained by replacing the phthalazinone as toning agent by one of the following compounds having one of the following structural formulae:

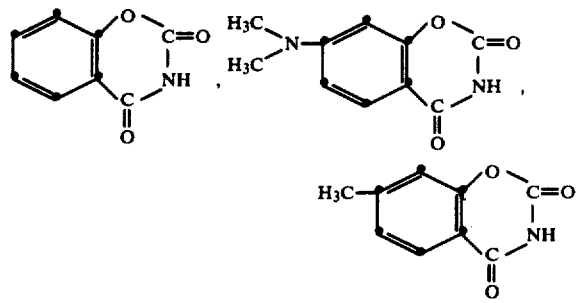

described in the German Patent Applications Nos. P 2,261,739 and P 2,328,145 as mentioned above.

According to the particular embodiment after the drying at 50° C. onto the dried layer a second layer was applied from a 3% solution in ethanol of ethylcellulose at a covering rate of 50 g per sq.m. After drying a more transparent material was obtained.

EXAMPLE 7

In a ball-mill the following ingredients were mixed for 8 h:

| | | |
|---|---|---|
| ethyl cellulose | 5 | g |
| silver behenate | 1.25 | g |
| 3-nitrophthalic acid | 0.025 | g |
| methyl ethyl ketone | 50 | ml |

To the obtained dispersion a solution containing 2 g of compound 17 (melting point 130° C.) and 0.4 g of phthalazinone in 50 ml of methyl ethyl ketone were added. The resulting mixture was coated on a paper base such as glassine paper at a covering rate of 150 g per sq.m.

After drying the recording material was held in contact with an information-wise modulated modulation-wise vibrating point of a stylus which was heated to a temperature of 220° C. and operating at a writing speed of 124 cm per min.

On the recording paper a dense black line track was obtained.

We claim:

1. A recording process, which comprises exposing to a heat pattern a support carrying an organic reducing compound corresponding to one of the following general formulae:

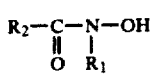

(I)

wherein:

$R_1$ represents hydrogen, an aliphatic group containing up to about four carbon atoms; and $R_2$ represents an alkoxy group containing up to 18 carbon atoms, an aryloxy group, an amino group of the formula

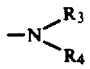

in which $R_3$ and $R_4$ (same or different) represent hydrogen, an aliphatic group or an aromatic group, or $R_3$ and $R_4$ represent together the necessary atoms to close a 5- or 6-membered heterocyclic nitrogen containing nucleus; and

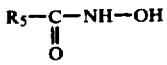

(II)

wherein:

[$R_5$ represents an aliphatic group containing up to 18 carbon atoms, an aromatic group or a 5- or 6-membered heterocyclic group;] *$R_5$ is an aromatic group,* and a reducible noble metal salt of an aliphatic carboxylic acid, said organic reducing compound being present in an effective amount to reduce said noble metal salt and said heat pattern having a temperature of at least about 60° C. and sufficient to initiate said reduction.

2. A recording process according to claim 1, wherein $R_2$ is the group

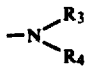

and $R_3$ and $R_4$ represent together the necessary atoms to close a piperidine nucleus.

3. A recording process according to claim 1, wherein $R_2$ is the group

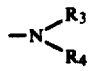

and $R_3$ represents hydrogen and $R_4$ an alkyl group.

4. A recording process according to claim 1, wherein the reaction partner is a noble metal salt which upon reduction yields free metal.

5. A recording process according to claim 1, wherein the reaction partner is a silver salt, which in the temperature range of 50° to 200° C. is generally non-light-sensitive.

6. A recording process according to claim 5, wherein the silver compound is a silver salt of an aliphatic carboxylic acid containing a thioether group.

7. A recording process according to claim 5, wherein the silver compound is a silver salt of an aliphatic carboxylic acid containing at least 13 carbon atoms.

8. A recording process according to claim 7, wherein the silver salt is silver behenate or silver stearate.

9. A recording process according to claim 4, wherein the organic reducing agent is used in an amount of at least 0.25 mole per mole of noble metal salt.

10. A recording process according to claim 1, wherein the organic reducing compound and noble metal salt are present in a sheet material and are heated information-wise in a temperature range of 60° to 200° C.

11. The process of claim 1, wherein said noble metal salt undergoes a visible color change when reduced.

* * * * *